United States Patent [19]

Sakuranaga et al.

[11] Patent Number: 5,882,917

[45] Date of Patent: Mar. 16, 1999

[54] METHOD FOR SURVIVAL OF FOREIGN MICROORGANISM AND METHOD FOR REMEDYING ENVIRONMENT BY USING IT

[75] Inventors: Masanori Sakuranaga, Atsugi; Kazumi Tanaka, Yokohama; Tsunehiro Kanno, Atsugi, all of Japan

[73] Assignee: Canon Kabushiki Kaisha, Tokyo, Japan

[21] Appl. No.: 926,484

[22] Filed: Sep. 10, 1997

Related U.S. Application Data

[63] Continuation of Ser. No. 367,428, Dec. 30, 1994, abandoned.

[30] Foreign Application Priority Data

Jan. 7, 1994 [JP] Japan ................................. 6-000528

[51] Int. Cl.$^6$ .............................. B09B 3/00; C02F 3/00; C12N 1/00; C12N 1/20
[52] U.S. Cl. ...................... 435/262; 435/243; 435/262.5; 435/822; 210/600; 210/601
[58] Field of Search ................. 435/243, 262.5, 435/822, 262; 210/600, 601

[56] References Cited

U.S. PATENT DOCUMENTS

| | | | |
|---|---|---|---|
| 4,259,317 | 3/1981 | Vesely et al. | 424/93.5 |
| 4,845,033 | 7/1989 | Tegtmeier | 435/162 |
| 5,232,850 | 8/1993 | Casida, Jr. | 435/253.3 |
| 5,653,675 | 8/1997 | Kanno et al. | 588/249 |

*Primary Examiner*—Herbert J. Lilling
*Assistant Examiner*—Deborah K. Ware
*Attorney, Agent, or Firm*—Fitzpatrick Cella Harper & Scinto

[57] ABSTRACT

A survival method for a foreign microorganism, which comprises the steps of disturbing the equilibrium state of an ecosystem in which plural kinds of microorganisms coexist, to temporarily bring the ecosystem into a non-equilibrium state, and then introducing a foreign microorganism into the ecosystem. There are three states of equilibrium involved of which comprise a first state wherein the ecosystem is in equilibrium, a second state wherein the ecosystem is converted to a state which is not in equilibrium, and a third state wherein the ecosystem is converted to a new state of equilibrium to provide for an ecological niche for survival of an introduced foreign microorganism in the ecosystem. The foreign microorganism is also used in a method for remedying an environment contaminated with a pollutant.

3 Claims, 3 Drawing Sheets

METHOD FOR SURVIVAL OF FOREIGN MICROORGANISM AND METHOD FOR REMEDYING ENVIRONMENT BY USING IT

This application is a continuation of application Ser. No. 08/367,428 filed Dec. 30, 1994, now abandoned.

BACKGROUND OF THE INVENTION

1. Field of the Invention

The present invention relates to a method for introducing and making foreign microorganisms survive in an ecological system such as waste water or soil in which various kinds of microorganisms coexist. More specifically, it relates to a method for survival of foreign microorganisms without replenishing the foreign microorganisms or nutrients, as well as a method to efficiently remedying the environment using the above-mentioned method in water treatment and soil remediation etc.

2. Related Background Art

In the field of waste water treatment, processes have been widely carried out to decompose target substances using activated sludge in which the activity of microorganisms is utilized. Furthermore, for the remediation of the polluted soil or polluted ground water, it has been attempted to introduce the microorganisms capable of degrading pollutants into the polluted area to remedy it.

The microorganisms, however, are generally passive to the environment and often sensitive to the given environment. They can not immediately adapt themselves to the given environment and the degradation activity is often lost or extinction may occur. In an ecosystem comprising plural kinds of microorganisms, it is observed that the niches of the ecosystem are already occupied by the various kinds of originally living microorganisms, and these native microorganisms do not easily permit the survival and growth of newly introduced foreign microorganisms.

In these cases, the foreign microorganism introduced into waste water or soil can not adapt to the new environment, and the population of the microorganism rapidly decreases resulting in little decomposition of a target substance. Otherwise, when the foreign microorganism adapts to the new environment at first, the population of the microorganism may decrease later due to the change of various environmental factors, so that the function of degradation and detoxification deteriorates or ceases to work entirely. For example, if a substance harmful to microorganisms is mixed into waste water, the activity of the activated sludge deteriorates and the target substance cannot be degraded any more. Even if the microorganisms having the degradation ability are newly introduced to restore the pollutant degradation ability of the activated sludge, it is difficult for the introduced microorganisms to squeeze themselves into the niches to live and grow, in the ecosystem already occupied by the various kinds of originally existing microorganisms.

If the target ecosystem is soil or the soil-water system including ground water, the interaction between the microorganisms and environmental components is stronger than in the activated sludge. Therefore, when the foreign microorganisms are introduced into such a system by an ordinary method, it is more difficult for the foreign microorganisms to stably grow in the ecosystem and maintain their concentration necessary for the degradation of the pollutants.

In order to compensate the reduction of the degradation microorganisms, usually the system such as a septic tank or soil is supplemented with an excessive amount of the degradation microorganisms to increase the amount of the decomposing microorganisms. Furthermore, in order to secure the good growth of the introduced microorganism, the ecosystem is replenished with components containing nutrients for the introduced microorganisms and oxygen gas to promote their growth and to increase the amount of the introduced microorganisms.

As stated above, when foreign microorganisms are introduced into an environment such as a septic tank or soil in this manner, there is a problem that the population of the introduced microorganisms decreases rapidly and as a result, the function of degradation and detoxification is lost. Supplementing the foreign microorganisms, nutrients, oxygen and the like as a measure to address this problem is time-consuming, and raises the cost when the foreign microorganisms and the nutrients are expensive. Moreover, since the reduction of the foreign microorganisms may occur at any moment, the population of the foreign microorganisms and the degradation ability of the microorganisms should be frequently measured to quantitatively determine the timing of replenishing the foreign microorganisms and the nutrients, and hence this method is very troublesome in practice.

SUMMARY OF THE INVENTION

In consideration of above discussed problems of conventional techniques, an object of the present invention is to provide a survival method for foreign microorganisms in an ecosystem without subsequent microbial or nutritional replenishment etc., which comprises, specifically treating the ecosystem where plural kinds of microorganisms coexist in an equilibrium state, prior to the introduction of the foreign microorganisms, so as to promote the survival and growth of the foreign microorganisms.

Another object of the present invention is to provide an efficient method for remedying the environment without heavily loading the environment, which comprises, based on the above survival method, introducing to an ecosystem foreign microorganisms which can convert certain substances for environmental remediation.

These objects can be achieved by the present invention.

The first aspect of the present invention is directed to a survival method for a foreign microorganism in an ecosystem containing a native microorganism occupying an ecological niche in said ecosystem and further the ecosystem is in a first state of equilibrium the foreign microorganism having an ecologically same or lower position to that of the native microorganism in the ecosystem, comprising (a) converting the ecosystem to a second state which is not in equilibrium by decreasing the population of the native microorganism by introducing into the ecosystem an ecologically higher biological species which preys on at least the native microorganism; and (b) introducing the foreign microorganism into the ecosystem in the second state and converting said ecosystem to a third state of equilibrium to provide for an ecological niche for said foreign microorganism in the ecosystem wherein the foreign microorganism survives within said ecological niche.

The second aspect of the present invention is directed to a process for introducing a foreign microorganism into an ecological niche in an ecosystem containing a native microorganism occupying an ecological niche and in a first state of equilibrium comprising:

(a) converting the ecosystem to a second state not in equilibrium by decreasing a population of the native microorganism by introducing into the ecosystem an ecologically higher biological species which preys on at least the native microorganism; and (b) introducing the foreign microorganism into the ecosystem in the second state, said foreign microorganism having an ecologically same or lower position to that of the native microorganism in the ecosystem, and converting the ecosystem to a third state of equilibrium by said introducing to provide for an ecological niche in the ecosystem wherein the introduced foreign microorganism occupies the ecological niche.

The third aspect of the present invention is directed to a method for remedying an environment contaminated with a pollutant using a foreign microorganism, the environment having an ecosystem containing a native microorganism and in a first state of equilibrium comprising:

(a) converting the ecosystem in the first state to a second state not in equilibrium by decreasing a population of the native microorganism by introducing into the ecosystem an ecologically higher biological species which preys on at least the native microorganism; and (b) introducing the foreign microorganism while the ecosystem is in the second state, said foreign microorganism having an ecologically same or lower position to that of the native microorganism in the ecosystem and further converting the ecosystem to a third state of equilibrium wherein the foreign microorganism increases in population and degrades the pollutant.

DETAILED DESCRIPTION OF THE PREFERRED EMBODIMENTS

Figure 1:
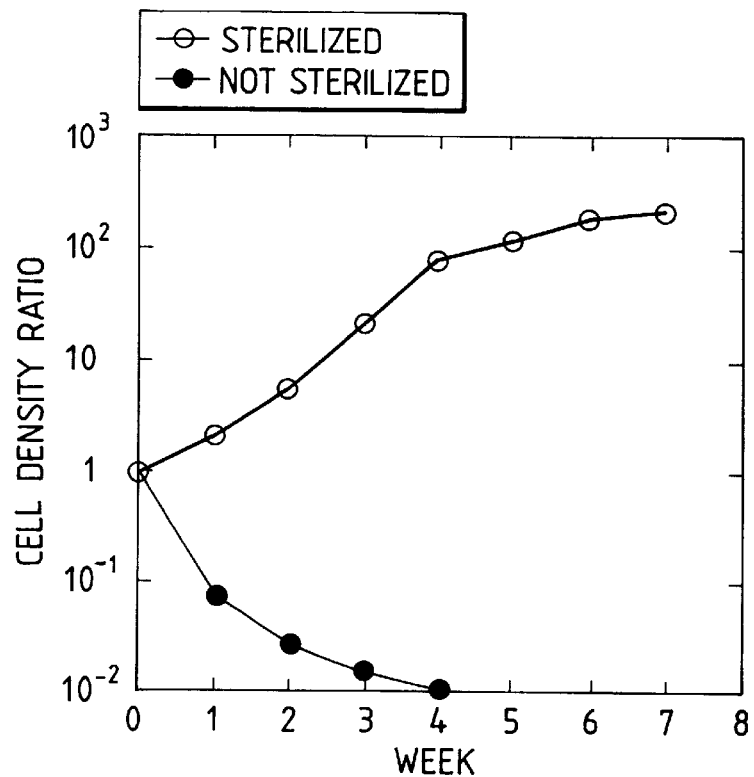
FIG. 1 shows the relation between time (weeks) and the survival counts of viable foreign microorganism in limitedly sterilized activated sludge and in unsterilized activated sludge expressed in cell density ratio (Example 1).

The present invention relates to a survival method for a foreign microorganism in an ecosystem, which comprises disturbing the equilibrium state of the ecosystem containing various coexisting microorganisms, temporarily shifting the ecosystem into a non-equilibrium state, and then introducing certain foreign microorganism into the ecosystem. When the equilibrium state of the ecosystem is temporarily disturbed prior to the introduction of the foreign microorganisms, the occupation state of the niches in the ecosystem comprising various native microorganisms is disturbed. Afterward, the foreign microorganism is introduced into the ecosystem in a non-equilibrium state, so that the introduced foreign microorganism can secure the niches in the ecosystem during the shift to a new equilibrium state, whereby the foreign microorganism can settle and survive dispensing with the further addition or replenishment of the foreign microorganisms, nutrients etc. after the introduction of the foreign microorganism.

The present invention also relates to a survival method for a foreign microorganism, in which disturbance of the ecosystem into a non-equilibrium state is carried out by decreasing the population of native microorganisms. The present invention is also concerned with a survival method for a foreign microorganism, in which the population of native microorganisms is reduced by limited sterilization of the ecosystem or the introduction of an ecologically higher biological species which preys on the microorganisms in the ecosystem.

The present invention is also concerned with a survival method for a foreign microorganism, wherein the ecosystem is temporally shifted from an equilibrium state into a non-equilibrium state by increasing the population of microorganisms. This means for increasing the population of the microorganisms may be, for example, the addition of growth promoting substances for the microorganisms.

By employing the above-mentioned means, the ecosystem is brought into a non-equilibrium state, whereby the foreign microorganisms can efficiently survive.

The present invention is also concerned with a method for remedying the environment, which comprises applying to an ecosystem one or more foreign microorganisms having a substance-converting ability useful to remedy the environment, using the above-mentioned survival method for the foreign microorganism. According to this method, the substance-converting ability of the foreign microorganism can be effectively utilized to degrade pollutants and the like, and therefore the polluted environment can be remedied rapidly and easily.

It is well known that many kinds of microorganisms coexist in activated sludge or soil establishing an ecosystem. The distribution of the microorganisms in such an ecosystem is supposed to be controlled by various factors, and one of these factors is the competition and symbiosis between the microorganisms. In other words, the population of a specific microorganism in a certain environment depends largely upon not only the physicochemical conditions of this environment but also the distribution of the other microorganisms. The present inventors have paid much attention to such interactions in the ecosystem, and found a novel survival method for foreign microorganisms to complete the present invention. The method is based on a principle quite different from the conventional methods comprising the addition or replenishment of the foreign microorganisms or nutrients. The microbial ecosystem is considered stable as a whole, maintaining substantially constant microbial distribution sometimes with periodical fluctuation in the relative population ratio or the respective absolute populations of the microorganisms, under the above-mentioned microbial interaction and certain physicochemical conditions. If a disturbance force which temporarily disturbs the equilibrium state is applied to the ecosystem in an equilibrium state, the balance of the interaction between the microorganisms is temporarily lost which disturbs the occupation state of various kinds of microorganisms in niches, and the ecosystem shifts to a non-equilibrium state, generating a pressure to shift in a new equilibrium state. During this process, if a foreign microorganism is introduced into the ecosystem, the ecosystem can provide room for the foreign microorganism, and the foreign microorganism can acquire the niches in the ecosystem establishing a new equilibrium state. This surprising discovery leads to the present invention.

The present invention will be described in more detail.

In the present invention, the ecosystem in which plural kinds of microorganisms coexist means a natural or an artificial environment in which a relative population ratio or the respective populations of the various kinds of microorganisms are maintained in an equilibrium state. Here, the microorganisms include fungi such as yeast, mold and mushroom, bacteria, actinomyces, single cell algae, viruses, protozoans, and undifferentiated cells or tissue cultures of animals or plants. For example, activated sludge used in the waste water treatment contains many kinds of microorganisms, and it maintains a certain equilibrium state, even though the state may fluctuate with time. A benefit of introducing a foreign microorganism to such a system is that when one or more microorganisms having a certain specific ability are newly introduced and survive in a septic tank, a specific substance present in the waste water can be degraded by the introduced microorganism and thus the ecosystem can be remedied. In particular, it is effective to keep a specific bacterium capable of degrading or adsorbing a barely decomposable organic compound in a septic tank for treating the waste water containing the barely decomposable organic compound.

The soil environment is also a microorganic ecosystem in which about 10,000 kinds of microorganisms of the total number of about 100,000,000 are thought to coexist in 1 g of soil. The purpose of introducing a foreign microorganism to such a system and keeping them alive is that a certain substance in the system may be newly converted by the specific microorganism introduced and surviving in the system. It is especially useful in detoxifying a pollutant in the soil using microorganisms.

In the present invention, the temporary change of the ecosystem into the non-equilibrium state is caused by changing the relative population ratio, or increasing or decreasing the absolute populations of the various kinds of microorganisms constituting the ecosystem, i.e., by disturbing the equilibrium state of the ecosystem. In the ecosystem in an equilibrium state, various microorganisms constituting the ecosystem have acquired and occupy inherent ecological niches.

In the present invention, the ecological niche means a living state of a certain microorganism or a certain microbial species, and it is secured in symbiosis and competition between the microorganisms, such as prey-predator relation between the microorganisms of higher and lower strata, or the food competition between the microorganisms of the same stratum. In addition to the interactions between the microorganisms, the microorganisms are directly affected by the factors of the ambient physicochemical environment. The physicochemical environment factors sharply affect the physiological activities of the microorganisms, while minute spaces in the soil masses, for example, provide living sites beneficial for the survival of certain microorganisms. As understood from the foregoing, the ecological niche in the present invention means the living state of a microorganism or a microbial species in the ecological environment including biological factors and physicochemical factors.

By changing the relative ratio of individual microorganisms, or increasing or decreasing the absolute populations of the microorganisms constituting the ecosystem, the system shifts to the non-equilibrium state, so that the microorganisms temporarily lose their ecological niches generating unoccupied ecological niches which other microorganisms can newly acquire. At this time, when foreign microorganisms are introduced into the ecosystem, competition occurs between the native microorganisms originally present in the ecosystem and the introduced foreign microorganisms for the vacant niches. However, the native microorganisms which have once lost the niches also lose their predominance over the foreign microorganisms more or less, in acquiring the niches in the ecosystem. When the foreign microorganisms are introduced in an ecosystem in an equilibrium state, they are expelled by the native microorganisms occupying the niches and cannot survive. Under the above-mentioned conditions, however, the foreign microorganisms can compete with the native microorganisms according to the adaptability to the physicochemical environment of the ecosystem to scramble for the niches, so that the survival probability of the foreign microorganisms increases.

In the present invention, as the means for changing the relative ratio of microbial populations or the absolute microbial population to bring the ecosystem into non-equilibrium state, techniques of various fields can be utilized. The utilizable technical fields include physics, physical chemistry, chemistry, biochemistry and biology. Both biological means and non-biological means are acceptable. Examples of the physical and physicochemical means are application of electric field or magnetic field; application of light such as infrared ray, visible light or ultraviolet light; application of radiation such as X ray, $\alpha$ ray or $\gamma$ ray; application of sound wave in the range from extremely low frequency to extremely high frequency, or mechanical vibration; application of thermal change or humidity change such as heating, cooling or dry-heating; disturbance by dynamic stirring; and physical substraction or deletion of a part of the system. Examples of the chemical and biochemical means are addition of metal salt compounds which can change the physiological activity of the microorganisms or affect the aqueous system and soil structure; addition of nutrients such as a saccharide, yeast extract, hydrolyzed protein such as peptone, and vitamins; and addition of a substance having suppressing or sterilizing activity to the microorganisms such as a protein denaturant, an oxidizing agent, an alkylating agent, a proteinase, a lipase, a surfactant or an organic solvent. Furthermore, as the biological means, protozoans which prey on bacteria can be added to the system, thereby disturbing the ecological equilibrium.

As recited above, in the present invention, any means can be employed, so long as it changes the relative population ratio or the absolute population of the various kinds of microorganisms to bring the ecosystem into the non-equilibrium state. Since this means is applied to an ecosystem, it affects both native and foreign microorganisms in the ecosystem. One means which suppresses the native microorganisms can also suppress the foreign microorganisms. Conversely, a means which propagates the foreign microorganisms can also propagate the native microorganisms. This fact does not deny the advantage of the present invention. In the present invention, by applying a means which temporarily brings the equilibrium ecosystem into the non-equilibrium state, the occupation state of the niches in the system is temporarily canceled, whereby the relative predominance of the native microorganisms over the foreign microorganisms is lost. An advantage of the present invention, is that the means of low cost and low load to the environment can be selected.

In the present invention, an easy means for bringing the ecosystem into the non-equilibrium state is to decrease or increase the total population of the microorganisms constituting the ecosystem. The natural ecosystem is constituted of tremendous kinds of microorganisms, and therefore it is difficult to species-specifically vary the number of microorganisms so as to control the population ratio of the microorganic species in the whole ecosystem. Thus, it is easy to apply a means which increases or decreases the population of microorganisms constituting the ecosystem. The response to one means may differ between microorganisms, one species may increase the population, one species may decrease the number, and the other species may not show any response. The absolute population of the microorganisms constituting the system may increase, decrease or not change, but in any case, the relative population of microbial species changes, so that the equilibrium of the system is disturbed. According to the purpose of the present invention, it is apparent that a means independently affects the native microorganisms and the foreign microorganisms, where the effects may be similar or opposite. Even if a certain means has a tendency of decreasing the population of the foreign microorganisms, it can give ecological niches to the foreign microorganisms and so it is useful as the survival method, so long as the means imparts some disturbance to the ecosystem consisting of the native microorganisms.

Furthermore, in the present invention, increase or decrease of the population of the microorganisms in the ecosystem includes the population change occurring locally or in the whole system. Decrease of the microbial population covers from complete extermination to very limited decrease. Here, the boundary of the objective ecosystem such as soil is not always definite, but in the present invention, the supposedly polluted area of the soil is defined as the range of the objective ecosystem. In the case of a septic tank, the range of the objective ecosystem is defined as the treatment carrier which is actually doing the waste water treatment.

When the microorganisms in the ecosystem are decreased, the degree of decrease should be suitably determined in consideration of the concentration of the microorganisms in the ecosystem, concentration of the foreign microorganisms to be introduced, desired concentration of settled foreign microorganism, difficulty of settlement for the foreign microorganisms (culture environment) and the like. So long as the population decrease of the microorganisms can disturb the equilibrium state of the ecosystem, the degree of population decrease may be restrictive. The distribution of microorganisms in an ecosystem tolerates changes to some extent, and when the very limited number of microorganisms perish, this change may be absorbed on the whole instead of transition to a new equilibrium state. Accordingly in the present invention, the decrease is carried out at a level causing disturbance. For example, in the case of soil, if the population of the microorganisms in the defined ecosystem is decreased to about 5 to 30% of the initial total population of the microorganisms, the equilibrium state is destroyed to such a degree as to allow the settlement of the foreign microorganisms. By using a means for sterilizing specified microorganisms, it is possible to decrease the specified microorganisms which are considered to competitively impede the survival of the foreign microorganisms. Furthermore, the reduction of the microbial population need not to be carried out over the whole range of a defined ecosystem, and reduction in a local range may be also satisfying. This local range means, for example, 5 to 30% of the whole range. The reduction rate of the microbial population in the local range is preferably the above-mentioned degree or such a degree that most of the microorganisms perish in that part. Practically, the above-mentioned limited sterilization is more preferable than the extermination of all the microorganisms. The degree of limited sterilization may be determined on the basis of the total viable cell number of the objective ecosystem. The limited sterilization is preferably carried out, for example, down to 5 to 30% of the initial viable count of the objective ecosystem.

In the ecosystem of a septic tank or soil, decomposition and detoxification are carried out by many microorganisms sharing the process, and the nutrients necessary for the microorganisms are in a material cycle among coexisting microorganisms. Therefore, the extermination of all the microorganisms in the ecosystem is not desirable since it makes the decomposition-detoxification function of this system imperfect and it also makes stable maintenance of microbial density impossible.

For the limited sterilization, various methods can be used. As a simple method, there is addition of a chemical agent. Examples of such a chemical agent include protein denaturants such as formalin, urea and carbolic acid; oxidizing agents such as hydrogen peroxide and halogens; alkylating agents such as ethyleneimine, ethylene oxide, nitrogen mustard and β-propiolactone; digestion enzymes such as trypsin, pronase, lipase and papain; organic solvents such as acetone, methyl alcohol and ethyl alcohol; surface active agents such as deoxycholic acid, lauryl sulfate salts, NP40 and Tween-80; and antibiotics such as penicillin, kanamycin and streptomycin. The usable agents are not limited to the recited substances, and any agent can be used, so long as it has a sterilization effect. Therefore, the agent suitable for the ecosystem can be selected in consideration of the resistance of the microorganism to be sterilized. In order to perform local sterilization by the use of such an agent, the agent is sprayed and diffused to a part of the objective ecosystem such as activated sludge or soil. Alternatively, the diluted agent can be sprayed and diffused.

It is also simple to apply a physicochemical treatment to the ecosystem. For example, dry heating treatment by exposing the ecosystem to flame or hot air; or wet heating treatment by boiling or steaming. In addition, a means such as freezing-thawing, pH change, salt concentration change or filtration can be used with ease. It is also effective to apply a physical means. Examples of the physical means include a mechanical treatment of applying sound waves, high pressure or surface tension change; the radiation treatment applying such as visible light or ultraviolet light; and the application of a radiation such as X ray, α ray or γ rays. The limited sterilization can be achieved by subjecting the objective ecosystem such as activated sludge or soil to the above-mentioned treatment. The strength or amount of the physicochemical or physical input of the above-mentioned treatment may be lessened, or the time of treatment may be shortened. This can be adjusted on the basis of common knowledge in the art.

As the biological means for decreasing the population of the microorganisms such as bacteria, there can be used protozoans belonging to a higher stratum than bacteria in a food chain of the ecosystem. The protozoans live in the aqueous system or soil of high water content and prosper on bacteria. Therefore, when protozoans is introduced to the microbial ecosystem, a prey-predator relation are formed between the protozoans and bacteria to disturb the equilibrium state of the ecosystem. It is known that particularly in the soil system, microorganisms inhabit in the soil structure such as soil aggregates to escape protozoan attack. Therefore, the microorganisms including the introduced foreign microorganism are not all eaten up by the added protozoans, but the equilibrium of the ecosystem is temporarily disturbed and shifts to another equilibrium state. The protozoans can be isolated from environment and cultured in large quantities, and they can suitably be used as the means for decreasing the bacterial population in the present invention.

Alternatively, by increasing the population of the native microorganisms in the ecosystem, it is possible to disturb the equilibrium of the system, and surprisingly, the occupation state of the ecological niches is temporarily disturbed, so that the introduced foreign microorganisms can acquire the niches by taking advantage it. In consequence, the survival ratio of the introduced foreign microorganism can be improved as compared with the foreign microorganism introduced without taking any means. The population of microorganisms can be achieved not only by adding nutrients necessary for the propagation of the microorganisms but also by optimizing the physicochemical growth environment for the microorganisms.

Examples of the main nutrients which accelerate the growth and propagation of the microorganisms include compounds containing carbon, nitrogen and phosphorus which are essential components constituting cells. Typical examples thereof include saccharides, aliphatic and aromatic hydrocarbons, amino acids, proteins and their hydrolyzed substances, and inorganic phosphate compounds. Coenzymes such as vitamins are also the nutrients in the present invention. Metallic salt compounds of potassium, sodium, calcium and the like are also the essential nutrients. Furthermore, when the native microorganisms are aerobic, oxygen or oxygen-releasing substances is essential to the microbial growth, thus included in the nutrients in the present invention.

Examples of the physicochemical environmental factors affecting the microbial growth include temperature, osmotic pressure, water content ratio, pH and oxidation-reduction potential. Each microbial species has its optimum environmental conditions, but the total population of the microorganisms in the system can be increased by selecting suitable conditions.

As in the case of decreasing the microbial population in the ecosystem, the same problems regarding the balance between disturbing equilibrium and maintaining the whole ecosystem arise when the microbial population is increased. That is to say, in the ecosystem of the septic tank or the soil, decomposition and detoxification are carried out by many microorganisms sharing the process, and the nutrients necessary for the microorganisms are in the material cycle among many coexisting microorganisms. Therefore, if microorganisms excessively propagate in the ecosystem, the ecosystem itself is ruined, so that it becomes impossible to utilize or activate the degradation and detoxification function of this system. In order to disturb the equilibrium of this system preventing such a disruption of the ecosystem, the above-mentioned nutrients are sprayed and diffused to a part of the objective ecosystem such as activated sludge or soil, or alternatively, nutrients may be diluted and sprayed in the same manner as in the limited sterilization, the strength or amount of the physicochemical or physical input of the above-mentioned treatment may be lessened, or the treatment time may be shortened. This can be adjusted on the basis of common knowledge in the art.

In the present invention, examples of the foreign microorganisms include yeast, mold, fungi, bacteria, actinomyces, single cell algae, virus, protozoa, undifferentiated cells and tissue culture of animals and plants. Considering practical use and benefit, bacteria and actinomyces are preferable. For example, there can be used bacteria of genus Pseudomonas which can be used to degrade organic compounds (e.g., petroleum hydrocarbons), and microorganisms belonging to the genera of Methylosinus, Methylomonas, Methylobacterium, Alcaligenes, Mycobacterium, Nitrosomonas, Xanthomonas, Spirillum, Vibrio, Bacterium, Acromobacter, Acinetobacter, Flavobacterium, Chromobacterium, Desulfotomaculum, Micrococcus, Sarcina, Bacillus, Streptomyces, Nocardia, Corynebacterium, Pseudobacterium, Arthrobacter, Bravibacterium, Saccharomyces and Lactobacillus which are known to have an ability capable of degrading various kinds of harmful substances.

As the foreign microorganism to be introduced, useful microorganisms are those having been isolated or those separated from the environment by screening in compliance with the purpose. A mixture of plural kinds of microorganisms is also usable. The microorganisms separated by screening need not to be identified. In addition, strains different from the wild type, obtained by mutation, fusion or genetic recombination may also be usable. The foreign microorganisms are not limited to the above-mentioned microorganisms, and any microorganism can be employed, so long as they are microorganisms which are not originally inhabiting in an environment such as the septic tank or the soil to which the microorganisms will be introduced. Further, the foreign microorganism in the present invention includes a pollutant-converting microorganism already present in the ecosystem to which the microorganism is introduced for environmental remediation. In the polluted ecosystem, it is known that the accumulation of microorganisms which metabolize the pollutant may often occur. When the population of such microorganisms is not sufficient enough to display the function, the microorganisms are once isolated and cultured to increase the population and are then reintroduced into the ecosystem. In that case, the survival method for the introduced microorganisms of the present invention is also effective, since the ecosystem in equilibrium state suppresses the increase of a specific microorganism even if the microorganism is originally indigenous to the system. In either case, to temporarily bring the ecosystem into a non-equilibrium state microorganisms are preferably employed which can settle and establish a new equilibrium state when they are introduced into the ecosystem system.

The cell number of the foreign microorganism to be introduced is properly determined based on the expected substance conversion ability of the microorganism, the concentration of the target substance to be degraded, or the like. Thus, it is preferable that prior to the actual introduction of the foreign microorganism, a test or experiment is carried out in a model system to obtain necessary values. Usually, though differs between microorganisms, the amount of the foreign microorganism to be introduced is in the range of $10^5$ to $10^{10}$ CFU, preferably $10^7$ to $10^{10}$ CFU per milliliter of the defined ecosystem. If the amount of the foreign microorganisms to be introduced is too small, the foreign microorganism can survive, but the degradation effect to the objective substance is scarcely observed. On the other hand, if the amount of the foreign microorganisms to be introduced is too large, shortage of the nutrients, rapid generation of anaerobic conditions and the like take place, so that the introduced microorganism noticeably decreases.

Thus introduced foreign microorganisms can settle and live, without further supplement of the microorganism or the nutrients to the ecosystem.

By using the above-mentioned survival method for the foreign microorganism, the environment can be effectively remedied by a means which gives little load to the environment. In this case, the effective foreign microorganism is one having a substance-converting ability necessary for the environmental remediation selected in compliance with the substance to be converted. Diluted or not diluted culture of the foreign microorganism is sprayed on the objective ecosystem, or it is mixed with the objective soil, or the foreign microorganism supported on a carrier may be sprayed. In view of the settlement efficiency of the microorganism, it is preferable that the foreign microorganism is supported on a carrier such as a clay mineral, activated carbon or a polymer.

Next, the present invention will be described in more detail with reference to examples. The scope of the present invention should not be limited to these examples.

EXAMPLE 1

E. coli HB101 was transformed with a kanamycin-chloramphenicol resistant vector pUSO800 by the calcium chloride method. The plasmid was prepared by the recombination between vectors pHSG298 and pHSG396.

10 ml of LB medium (10 g/l of bactopeptone, 5 g/l of yeast extract and 10 g/l of sodium chloride; pH=7.5) was inoculated with the transformant, and cultured with shaking at 37° C. until the logarithmic growth phase.

Next, 100 g of activated sludge was placed in a flask, and 10 ml of an aqueous solution of 3% hydrogen peroxide was added thereto. The mixture was kept standing for 2 hours to limitedly sterilize the activated sludge. Before and after this sterilization, the number of the bacteria was calculated by the plate dilution method, and as a result, the number of the microorganisms in this ecosystem was decreased to about 30% of the initial population (the number of living bacteria= about $6 \times 10^8$ CFU/g sludge). Afterward, 10 ml of LB medium inoculated with the previously prepared E. coli HB101 was added, followed by mild shaking. A sample (1 g) was taken out from this activated sludge every week, and plated on kanamycin containing plates, then the number of E. coli was calculated. As a result, the viable cell number of E. coli HB101 one week after the introduction of E. coli was about $10^7$ CFU/g sludge, and afterward, the E. coli concentration was substantially constant over 7 weeks, whereby it was confirmed that E. coli which was foreign to the ecosystem was surviving in the ecosystem.

As a comparative example, 100 g of the activated sludge was inoculated with above E. coli HB101, and the number of colonies of E. coli was counted every week in the same manner to monitor the concentration of the viable cells. As a result, it was confirmed that the cell concentration decreased week after week. FIG. 1 shows the results of the example and the comparative example for comparison. From these results, it was confirmed that in the activated sludge limitedly sterilized with hydrogen peroxide, the E. coli concentration increased apparently and they stably survive.

EXAMPLE 2

To 200 g of an andosol, 100 ml of a 3% hydrogen peroxide aqueous solution was added dropwise, and the mixture was then allowed to stand for about 2 hours to be restrictively sterilized, whereby the microbial population was decreased to about 5% of the initial population ($3 \times 10^8$/g soil) of the bacteria. A glass column was packed with this soil sample, and the soil column was inoculated from its upper surface with E. coli HB101 prepared by the same procedure as in Example 1. Afterward, LB medium was added to the column to immerse the soil, and the column was then moderately shaken.

The concentration of E. coli in the soil sample was measured every week in the same manner as in Example 1. As a result, the number of E. coli one week after the introduction of E. coli was about $2 \times 10^6$ CFU/g soil, and afterward, the E. coli concentration was substantially constant over 7 weeks, whereby it was confirmed that E. coli which was foreign to the system was alive in it.

Figure 2:
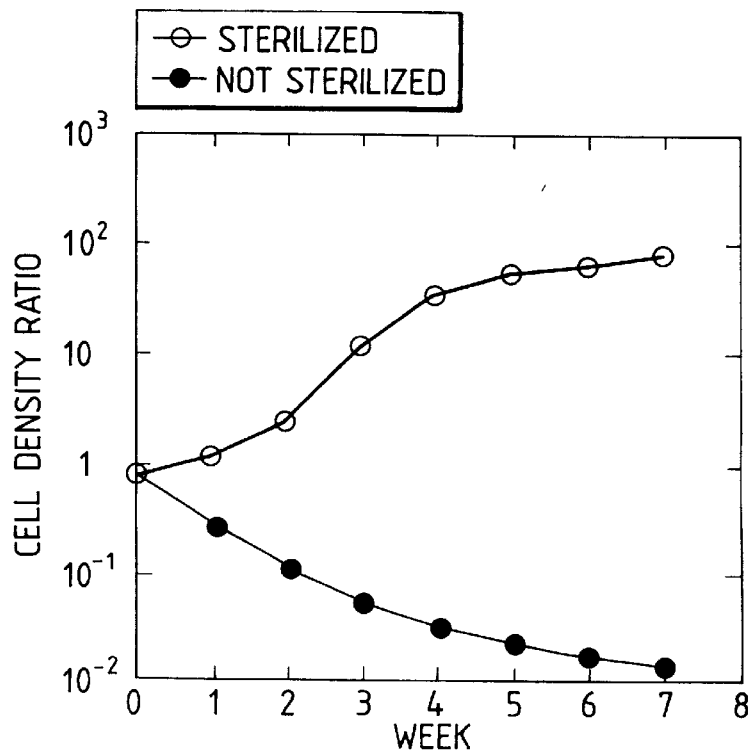
FIG. 2 shows the relation between time (weeks) and the survival counts of foreign microorganism in limitedly sterilized soil and in unsterilized soil expressed in cell density ratio (Example 2).

As a comparative example, a glass column was filled with 200 g of the same andosol as above without treating the soil with hydrogen peroxide. Then it was inoculated with HB101 similarly and E. coli concentration was measured. FIG. 2 shows the results of the example and the comparative example for comparison. From these results, it was confirmed that in the soil subjected to the hydrogen peroxide treatment, E. coli increased in concentration and they were stably alive.

EXAMPLE 3

10 ml of M9 medium containing 0.05% of phenol was inoculated with Pseudomonas cepacia KK01 (Biotechnology Research Institute, Agency of Industrial Science and Technology, Ministry of International Trade and Industry, Deposition No. FERM BP-4235), and cultured until O.D. became about 0.7.

As a test soil, 200 g of andosol was prepared and 100 g of it was dried at 120° C. for 1 hour for sterilization. Next, the thus sterilized soil was mixed with the remaining sample (the number of the bacteria decreased down to about 30%), and it was then immersed in M9 medium. Further 1000 ppm phenol was diffused to prepare phenol-polluted soil. The polluted soil was then inoculated with 10 ml of the previously prepared KK01 suspension.

The phenol concentration of the soil was determined by HPLC, and phenol residue ratio was then calculated, making the initial phenol concentration=1. As a result, the phenol residue ratio one week after the introduction of the KK01 strain was about 0.62. Afterward, the phenol residue ratio decreased over 5 weeks, whereby it was confirmed that the KK01 strain which was foreign settled and survived gradually degrading phenol in the ecosystem.

Figure 3:
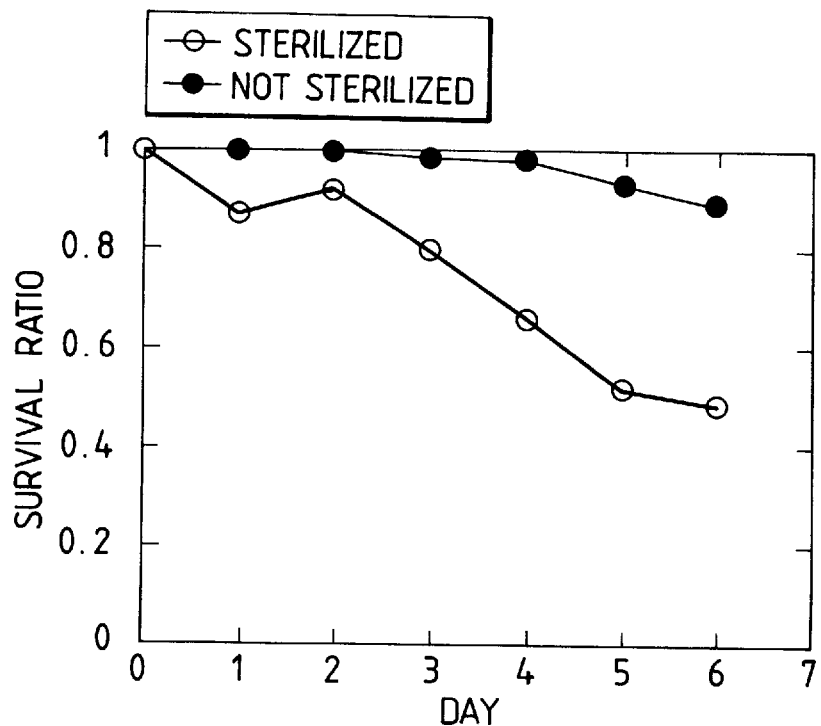
FIG. 3 shows the relation between time (days) and the amounts of residual phenol in limitedly sterilized soil and in unsterilized soil expressed in residual ratio (Example 3).

As a comparative example, 200 g of the test soil was immersed in M9 medium without sterilizing, and 1000 ppm phenol was diffused to prepare a polluted soil sample. The polluted soil sample was similarly inoculated with KK01 strain. Change of the phenol concentration was measured in the same manner as above example, and this change is shown in FIG. 3, for comparison. It was confirmed from the results that the phenol removal efficiency becomes high when the restrictive sterilization was done.

EXAMPLE 4

In 300 ml vial, M9 medium containing 3 ppm trichloroethylene (TCE), 50 ppm phenol and 0.05% yeast extract was placed. An andosol sample which was restrictively sterilized in the same manner as described in Example 3 was added to the vial up to the surface of the medium, and then it was inoculated with 0.1 ml of KK01 culture. Afterward, the vial was sealed with a butyl rubber plug and an aluminum seal, and it was incubated at 30° C.

Figure 4:
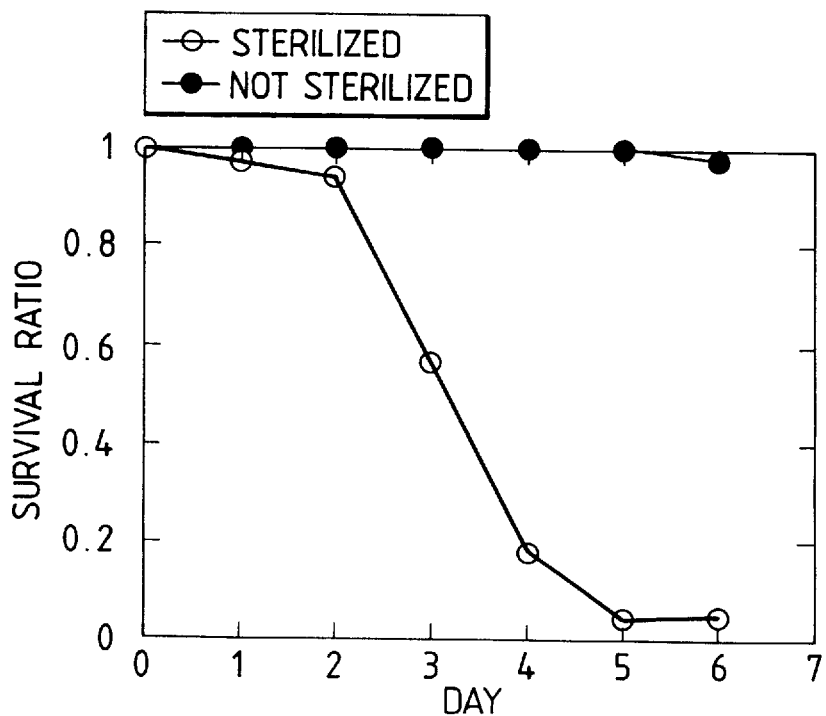
FIG. 4 shows the relation between time (days) and the amounts of residual trichloroethylene and in limitedly sterilized soil and in unsterilized soil (Example 4).

At a predetermined culture period (days), TCE content in the vial was determined by the head space method using gas chromatography, and the TCE residue ratio was calculated. As a comparative example, the andosol sample which was not subjected to sterilization treatment was put in a vial in the same manner as in the above example and the TCE residue ratio was measured. In FIG. 4, the results of the example and comparative example are shown. It was confirmed from these results that the TCE removal efficiency was high when the restrictive sterilization was done.

EXAMPLE 5

Figure 5:
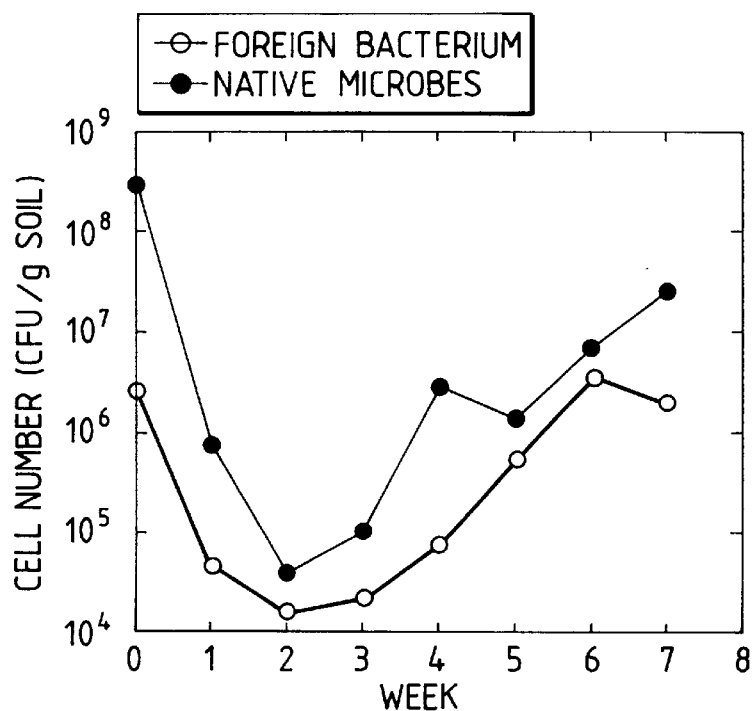
FIG. 5 shows the relation between time (weeks) and the population of introduced foreign bacterium and the number of native bacteria in the soil supplemented with protozoans (Example 5).

Colpodas which is a protozoa belonging to ciliates was collected from an outdoor canal and then cultured and propagated. Next, a glass column was filled with 200 g of untreated andosol, and the soil was inoculated from the upper surface of the column with 50 ml of LB medium containing 100 Colpodas/ml and *E. coli* HB101 prepared by the same manner as in Example 1 to immerse the soil. Afterward, it was moderately shaken at room temperature. The number of *E. coli* and the number of native bacteria in the soil sample were counted every week. The results are shown in FIG. 5.

Immediately after the introduction of Colpodas and *E. coli*, the number of the native bacteria and the number of the introduced *E. coli* were rapidly decreased by the predation of the Colpodas, but the activity of the Colpodas lowered according to the decrease of the bacterial population which are the prey for the Colpodas in the system, so that the population of the total bacteria in the system increased again and the system reached an equilibrium state, where the introduced foreign *E. coli* acquired niches, and it was confirmed that the *E. coli* concentration of about $2 \times 10^6$ CFU/g soil was maintained.

EXAMPLE 6

In a flask, 100 g of activated sludge was placed and the number of native bacteria was counted as about $6 \times 10^8$ CFU/g sludge. Afterward, the sludge was inoculated with about $2 \times 10^4$ CFU of *E. coli* HB101 prepared in the same manner as in Example 1, and 10 ml of LB medium of five-fold concentration was added as nutrients for both the native and foreign bacteria and cultured with vigorous shaking so as to feed oxygen. From this activated sludge, a sample (1 g) was taken every day, and plated on LB plates containing or not containing kanamycin. Afterward, the numbers of *E. coli* and the native bacteria were calculated.

As a result, after the introduction of the foreign bacteria, the native bacteria and later the foreign bacteria started propagation, and after 4 days, the number of the foreign *E. coli* became $10^7$ CFU/g sludge. After that, the concentration of the bacteria was substantially constant over 7 days and the system was in an equilibrium state. Thus, it was confirmed that foreign *E. coli* was surviving.

As a comparative example, the experiment was carried out except that nutritious culture medium was not added and during culture shaking was moderately conducted to restrict the oxygen supply. In this experiment, the number of the introduced *E. coli* was as small as $10^2$ CFU/g sludge after 7 days, and thus an effective survival could not be attained.

EXAMPLE 7

Andosol was collected from outdoor soil and an aliquot of 200 g was packed in a glass vessel. At the sampling time, the soil temperature was 16° C. and the number of microorganisms in the soil was $3 \times 10^8$ CFU/g soil. *Pseudomonas cepacia* KK01 (Biotechnology Research Institute, Agency of Industrial Science and Technology Deposition Number FERM BP-4235) was grown in 2×YT medium containing 5% sodium glutamate and 5 ml of the culture (ca. $10^6$ CFU) was added to the soil in the vessel. The vessel was left standing in an incubator kept at 30° C., and every one week, a sample was taken to determine the number of indigenous and foreign microorganisms. *P. cepacia* KK01 can grow on phenol as a sole carbon source and the number of *P. cepacia* KK01 can be estimated by the plate dilution method using a selective phenol medium and by the colony morphology.

During incubation, the number of microorganisms in the soil increased due to the temperature rise, and the number of the native microorganisms became as high as $6 \times 10^9$ CFU/g soil after three weeks incubation. On the other hand, the number of foreign microorganism, *P. cepacia* KK01 was only $2 \times 10^3$ CFU/g soil after one week incubation, but reached $7 \times 10^8$ CFU/g soil after three weeks incubation.

After three weeks incubation, the vessel was moved to another incubator kept at 15° C., and the number of the microorganisms were further monitored. Because of the temperature lowering and the consumption of nutrients with time lapse, the cell number began to decline. After five weeks of incubation, the numbers of indigenous and foreign microorganisms were $2 \times 10^7$ CFU/g soil and $6 \times 10^6$ CFU/g soil respectively.

As a comparative example, a vessel was incubated at 15° C. throughout the experiment without the incubation at 30° C. In this vessel, the number of indigenous microorganisms in the soil did not change and the number of the introduced *P. cepacia* KK01 was $3 \times 10^2$ CFU/g soil after two weeks incubation and after five weeks incubation only ca. $10^2$ CFU/g soil. As a result, introduced *P. cepacia* KK01 could not acquire the niches occupied by the indigenous microbes and could not survive at the effective concentration to decompose the pollution substance. This result shows that the disturbance of the equilibrium of the ecosystem (in this case, with the temporal high temperature incubation) is effective for the introduction and survival of a foreign microorganism.

EXAMPLE 8

In the vessel of above comparative example of Example 7, the number of *P. cepacia* KK01 became ca. $10^2$ CFU/g soil, an insufficient survival concentration, after five weeks incubation. When the vessel was successively incubated for another 8 weeks, however, the number of *P. cepacia* KK01 was still $9 \times 10$ CFU/g soil. At that time, the total number of indigenous microbes was $8 \times 10^7$ CFU/g soil. At this point, it is thought that *P. cepacia* KK01 is living as an indigenous microorganism in the test soil although the concentration is very low. To this system, further introduction of *P. cepacia* KK01 culture accompanied with system disturbance was carried out to increase the cell concentration to the level sufficient enough to decompose the pollution substance.

*Pseudomonas cepacia* KK01 (Biotechnology Research Institute, Agency of Industrial Science and Technology Deposition Number FERM BP-4235) was grown in 2×YT medium containing 5% sodium glutamate. Two hundred grams of the above mentioned soil sample containing a small number of *P. cepacia* KK01 was limitedly sterilized by spraying 10 ml of 0.1% sodium hypochlorite solution to the sample and leaving it stand for two hours. The microorganisms in the soil decreased by 25% of the starting viable count ($8 \times 10^7$ CFU/g soil). This soil sample was packed in a glass column, to which 10 ml of the *P. cepacia* KK01 culture of $4 \times 10^7$ CFU/ml 2×YT medium was added to the upper surface of the soil followed by gentle shaking. The number of P. cepacia KK01 was counted every one week. As a result, the number of P. cepacia KK01 became $3\times10^7$ CFU/g soil after one week of incubation, and continuously increased to reach $6\times10^9$ CFU/g soil after five weeks incubation and after that the growth became stationary.

Figure 6:
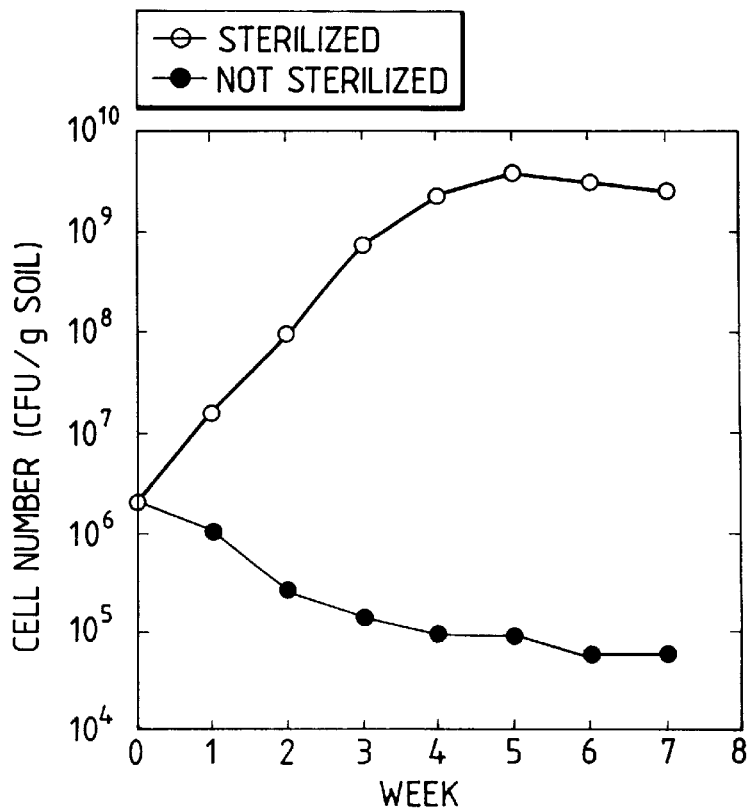
FIG. 6 shows the relation between time and the cell density in limitedly sterilized soil, and in unsterilized soil (Example 8).

As a comparative example, the same sample column was prepared and inoculated by P. cepacia KK01 except that the sterilization was not done, and the number of P. cepacia KK01 was counted every week. The results of this Example 8 and comparative Example are shown in FIG. 6. It was confirmed that because of the partial sterilization newly introduced P. cepacia KK0l was accepted and could grow and survive in the ecosystem in which P. cepacia KK0l had been surviving at a concentration as low as $9\times10$ CFU/g soil.

As described above, according to the present invention, in introducing foreign microorganisms to an ecosystem in which plural microbial species coexist in an equilibrium state, there is taken a means for changing the relative population ratio or the absolute population of the various kinds of microorganisms, i.e., a means for disturbing the equilibrium of the ecosystem to temporarily bring the ecosystem into a non-equilibrium state, whereby the foreign microorganism can survive and propagate without any subsequent replenishment.

By decreasing or increasing the population of the microorganisms in the ecosystem, survival of the foreign microorganisms can be efficiently achieved.

According to the above-mentioned survival method, the substance conversion ability of a foreign microorganism can efficiently be utilized without heavy burden to the environment, whereby the remediation of the environment can be carried out rapidly and with less labor.

According to the present invention, a foreign microorganism can stably survive in a sufficient amount in an ecosystem such as activated sludge or soil in which many kinds of microorganisms coexist. Thus, the substance conversion ability of the foreign microorganism can be utilized to promptly remedy the environment, and the replenishment of the microorganism in compensation for the decrease of the microorganism as well as frequent measurement of the concentration and the activity of the microorganisms can be lessened.

What is claimed is:

1. A survival method for a foreign microorganism in an ecosystem containing a native microorganism occupying an ecological niche in said ecosystem and further said ecosystem is in a first state equilibrium, the foreign microorganism having an ecologically same or lower position to that of the native microorganism in the ecosystem, comprising:

(a) converting the ecosystem to a second state which is not in equilibrium by decreasing the population of the native microorganism by introducing into the ecosystem an ecologically higher biological species which preys on at least the native microorganism; and (b) introducing the foreign microorganism into the ecosystem in the second state and converting said ecosystem to a third state equilibrium to provide for an ecological niche for said foreign microorganism in the ecosystem wherein the foreign microorganism survives within said ecological niche.

2. A process for introducing a foreign microorganism into an ecological niche in an ecosystem containing a native microorganism occupying an ecological niche and in a first state of equilibrium comprising:

(a) converting the ecosystem to a second state not in equilibrium by decreasing a population of the native microorganism by introducing into the ecosystem an ecologically higher biological species which preys on at least the native microorganism; and (b) introducing the foreign microorganism into the ecosystem in the second state, said foreign microorganism having an ecologically same or lower position to that of the native microorganism in the ecosystem, and converting the ecosystem to a third state of equilibrium by said introducing to provide for an ecological niche in the ecosystem wherein the introduced foreign microorganism occupies the ecological niche.

3. A method for remedying an environment contaminated with a pollutant using a foreign microorganism, the environment having an ecosystem containing a native microorganism and in a first state of equilibrium comprising:

(a) converting the ecosystem in the first state to a second state not in equilibrium by decreasing the population of the native microorganism by introducing into the ecosystem an ecologically higher biological species which preys on at least the native microorganism; and (b) introducing the foreign microorganism while the ecosystem is in the second state, said foreign microorganism having an ecologically same or lower position to that of the native microorganism in the ecosystem and further converting the ecosystem to a third state of equilibrium, wherein the foreign microorganism increases in population and degrades the pollutant.

* * * * *

UNITED STATES PATENT AND TRADEMARK OFFICE
CERTIFICATE OF CORRECTION

PATENT NO. : 5,882,917

DATED : March 16, 1999

INVENTOR(S) : MASANORI SAKURANAGA, ET AL.   Page 1 of 3

It is certified that error appears in the above-identified patent and that said Letters Patent is hereby corrected as shown below:

On the title page:

AT [56] REFERENCES CITED

Under Attorney, Agent, or Firm, "Fitzpatrick Cella Harper & Scinto" should read --Fitzpatrick, Cella, Harper & Scinto--.

COLUMN 1

Line 16, "to" should read --for--; and
    Line 26, "the" should be deleted.

COLUMN 2

Line 30, "comprises," should read --comprises--;
    Line 46, "equilibrium" should read --equilibrium,--; and
    Line 48, "ecosystem, comprising" should read
--ecosystem   --comprising.--.

COLUMN 3

Line 27, "equilibrium" should read --equilibrium,--;
    Line 50, "time" should read --time (weeks)--; and
    Line 62, "microorganism" should read --microorganisms--.

COLUMN 4

Line 20, "temporally" should read --temporarily--; and
    Line 45, "certain" should read --specific--.

COLUMN 6

Line 33, "substraction" should read --subtraction--; and
    Line 63, "invention," should read --invention--.

UNITED STATES PATENT AND TRADEMARK OFFICE
CERTIFICATE OF CORRECTION

PATENT NO. : 5,882,917

DATED : March 16, 1999

INVENTOR(S) : MASANORI SAKURANAGA, ET AL.

It is certified that error appears in the above-identified patent and that said Letters Patent is hereby corrected as shown below:

COLUMN 7

Line 3, "tremendous" should read --enormous--;
    Line 48, "the" should read --a--; and
    Line 62, "to" should be deleted.

COLUMN 8

Line 62, "are" should read --is--.

COLUMN 9

Line 13, "advantage it." should read --advantage of it.--.

COLUMN 10

Line 12, "Bravibacterium," should read --Brevibacterium,--;
    Line 20, "to" should be deleted;
    Line 45, "tem system." should read --tem.--; and
    Line 53, "differs" should read --it differs--.

COLUMN 14

Line 60, "above mentioned" should read --above-mentioned--.

COLUMN 15

Line 49, "is" should read --being-- and "equilibrium," should read --of equilibrium,--.

UNITED STATES PATENT AND TRADEMARK OFFICE
CERTIFICATE OF CORRECTION

PATENT NO. : 5,882,917

DATED : March 16, 1999

INVENTOR(S) : MASANORI SAKURANAGA, ET AL.   Page 3 of 3

It is certified that error appears in the above-identified patent and that said Letters Patent is hereby corrected as shown below:

<u>COLUMN 16</u>

Line 10, "equilibrium," should read --of equilibrium,--; and
    Line 44, "ecosystem" should read --ecosystem,--.

Signed and Sealed this

Twenty-eighth Day of December, 1999

Attest:

Q. TODD DICKINSON

*Attesting Officer*   *Acting Commissioner of Patents and Trademarks*